United States Patent [19]
Prakash

[11] Patent Number: 5,585,464
[45] Date of Patent: Dec. 17, 1996

[54] RECOMBINANT ANTIGEN FOR DIAGNOSING RHEUMATOID ARTHRITIS

[75] Inventor: Ramesh K. Prakash, Salt Lake City, Utah

[73] Assignee: Theratech, Inc., Salt Lake City, Utah

[21] Appl. No.: 364,081

[22] Filed: Dec. 27, 1994

Related U.S. Application Data

[63] Continuation-in-part of Ser. No. 19,780, Feb. 19, 1993, Pat. No. 5,395,753.

[51] Int. Cl.⁶ .......................... C07K 14/435; G01N 33/53
[52] U.S. Cl. .............................. 530/350; 435/7.1; 436/547
[58] Field of Search ................................................ 530/350

[56] References Cited
PUBLICATIONS

Burg et al., J. Immunol. 141:3584–3591 (1988).

*Primary Examiner*—Robert A. Wax
*Assistant Examiner*—Eric Grimes
*Attorney, Agent, or Firm*—Thorpe, North & Western, L.L.P.

[57] ABSTRACT

A method is described for diagnosing rheumatoid arthritis by providing a recombinant antigen (RAMA) and detecting rheumatoid arthritis-associated IgM antibodies against the RAMA antigen in patient sera. The RAMA antigen comprises SEQ ID NO:3 and peptides substantially homologous thereto. A purified and isolated DNA encoding the RAMA antigen and a transformed host containing the DNA are also disclosed.

7 Claims, 1 Drawing Sheet

RECOMBINANT ANTIGEN FOR DIAGNOSING RHEUMATOID ARTHRITIS

BACKGROUND OF THE INVENTION

This is a continuation-in-part of application Ser. No. 08/019,780, filed Feb. 19, 1993, now U.S. Pat. No. 5,395,753.

This invention relates to a method for diagnosing rheumatoid arthritis. More particularly, this invention relates to a method for objectively diagnosing rheumatoid arthritis by quantitative determination of the presence or absence of rheumatoid arthritis-associated antibodies in patient sera that react with a recombinant antigen. The invention also relates to the recombinant antigen and a molecular clone of the gene thereof.

Rheumatoid arthritis is a chronic systemic rheumatic disease that affects a significant percentage of the population. Traditionally, it has been diagnosed subjectively through clinical observation and dominant complaints by a patient. P. Lipsky, *Rheumatoid Arthritis,* in Harrison's Principles of Internal Medicine 1423 (1987). Thus, clinical diagnosis of rheumatoid arthritis is subject to the skill of the diagnostician and the severity of disease symptoms in the patient.

For an objective diagnosis of rheumatoid arthritis, the presence of rheumatoid factor (Rf) in the serum of rheumatoid arthritis patients is routinely determined. Rf is an autoantibody that binds to the constant region of IgG immunoglobulins. The standard test for determining the presence of Rf in blood is an aggregation test wherein Rf causes aggregation of IgG. Rf has been detected in approximately 70% of patients exhibiting clinical symptoms of rheumatoid arthritis. These patients are thus termed "seropositive." The remaining 30% are classified as having "seronegative" rheumatoid arthritis. Numerous conditions besides rheumatoid arthritis are associated with the presence of rheumatoid factor. Therefore, the presence of Rf does not establish a conclusive diagnosis of rheumatoid arthritis. An objective method of diagnosing rheumatoid arthritis that is more closely correlated with clinical diagnoses than is the presence of Rf in sera is needed. Ideally, such an objective diagnostic test would be quick and easy to perform and would not involve radioisotopes or be invasive to the patient.

Sera from patients with various autoimmune rheumatic diseases contain circulating autoantibodies that are directed against cellular, mainly nuclear, components. E. Tan, 33 Advances in Immunology 167–240 (1982). These antibodies, designated as antinuclear antibodies (ANA), are specific for their respective autoimmune diseases and have been useful as diagnostic aids in clinical medicine. Some of the antigens against which these antibodies are directed have been produced by methods of biotechnology and used in diagnosis of respective autoimmune diseases. R. Michael & J. Keene, *Molecular Biology of Nuclear Autoantigen,* in 18 Rheumatoid Disease Clinics of North America 283–310 (D. Pisetsky, ed., 1992). Success in developing diagnostic tests against these autoimmune diseases suggests that a similar approach might be fruitful for rheumatoid arthritis.

Sera from rheumatoid arthritis patients have also been found to contain antibodies to cellular components. A precipitin line forms in agar gel diffusion tests when sera from rheumatoid arthritis patients and extracts of certain Epstein-Barr virus-transformed human B lymphocyte cell lines, such as the WIL-2 and Raji cell lines, are placed in adjacent wells. M. Alspaugh & E. Tan, 19 Arthritis and Rheumatism 711–19 (1976). The antibody responsible for the precipitate is of the IgG type and the antigen against which it reacts is a nuclear antigen. Thus, the antigen is termed "rheumatoid arthritis nuclear antigen" or "RANA."

Several problems would need to be overcome before a diagnostic test based on the presence of RANA could be developed. The identity of the antigen is not known. Even if it were known, it occurs in small quantities in cells and would be difficult to purify to homogeneity. Such purity is needed because false positives might result if contaminants were copurified with the RANA, given the extreme sensitivity of serological tests that can be devised to detect small quantities of antigen.

For these reasons, the present invention discloses a different approach to quantitative detection of rheumatoid arthritis. This approach involves production of a recombinant antigen by recombinant DNA technology and detection of rheumatoid arthritis-associated antibodies to this novel antigen in patient sera. This recombinant antigen does not react with commercial anti-RANA antibodies.

OBJECTS AND SUMMARY OF THE INVENTION

It is an object of the present invention to provide a method for diagnosing rheumatoid arthritis.

It is another object of the invention to provide a method for diagnosing rheumatoid arthritis by serological analysis of patient sera, such as by ELISA analysis.

It is also an object of the invention to provide a nucleic acid capable of directing expression of a recombinant antigen detectable by rheumatoid arthritis-associated antibodies.

It is still another object of the invention to provide a recombinant antigen detectable by rheumatoid arthritis-associated antibodies.

These and other objects may be accomplished by providing an antigen for diagnosing rheumatoid arthritis comprising a peptide having an amino acid sequence selected from the group consisting of SEQ ID NO:3 and sequences substantially homologous thereto, wherein the antigen is reactive with rheumatoid arthritis-associated antibodies. The antigen can be expressed in prokaryotic or eukaryotic host cells or can be synthesized chemically. The rheumatoid arthritis-associated antibodies are of the IgM subtype.

The invention also comprises a purified and isolated DNA for use in securing expression in a host cell of a peptide having at least a part of the primary structural conformation and the antigenic activity of naturally-occurring RAMA protein; the DNA selected from the group consisting of:

(a) SEQ ID NO:2;

(b) DNA that hybridizes to SEQ ID NO:2 or fragments thereof; and (c) DNA that, but for the degeneracy of the genetic code, would hybridize to the DNA defined in (a) and (b). The purified and isolated DNA can further comprise a vector adapted for transformation of a host, wherein the vector is selected from the group consisting of plasmids, cosmids, phagemids, phages, viruses, and the like. The host can be a prokaryotic cell, such as *E. coli,* or a eukaryotic cell.

DETAILED DESCRIPTION

Figure 1:
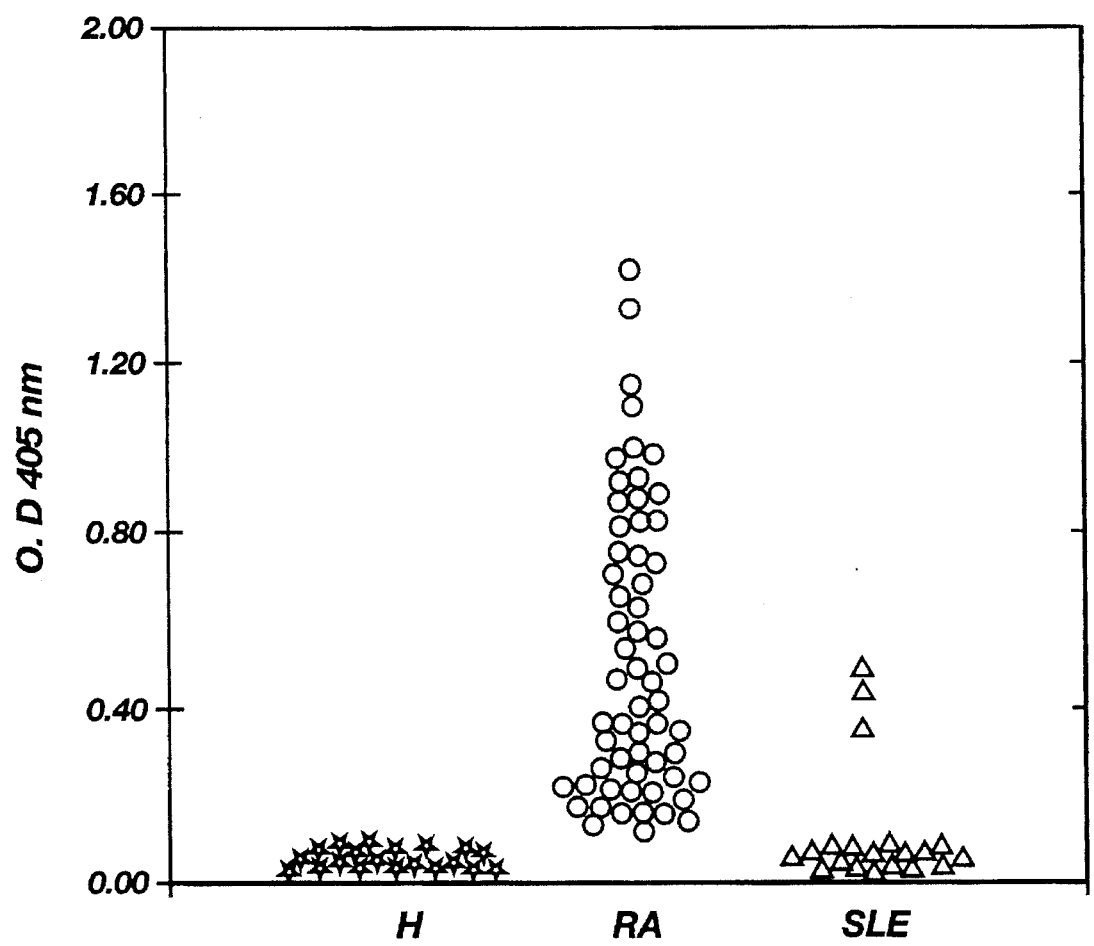
FIG. 1 is a graph depicting the results of ELISA tests of sera from healthy (H), rheumatoid arthritis (RA), and systemic lupus erythematosus (SLE) sera according the present invention.

Before the present recombinant antigen and molecularly cloned gene thereof are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the content clearly dictates otherwise. Thus, for example, reference to an antigen containing "a peptide" includes a mixture of two or more peptides, reference to "a host cell" includes reference to one or more of such host cells, and reference to "a plasmid" includes reference to a mixture of two or more plasmids.

In describing and claiming the present invention, the following terminology will be used in accordance with the definitions set out below.

As used herein, "RAMA" means the Rheumatoid Arthritis IgM-associated Antigen of the instant invention, encoded by the plasmid deposited as ATCC 69605.

As used herein, "peptide" means peptides of any length and includes proteins. The terms "polypeptide" and "oligopeptide" are used herein without any particular intended size limitation, unless a particular size is otherwise stated.

As used herein, "DNA" means DNA and other nucleic acids capable of storing genetic information. For example, an RNA produced by in vitro transcription of a RAMA gene is included within the scope of the term DNA.

As used herein, "vector" means any genetic element capable of replicating in a host cell and of carrying foreign nucleic acid that is inserted into the vector. Illustrative of vectors that can be used within the scope of the invention are plasmids, cosmids, phagemids, phages, viruses, and the like.

As used herein, "substantially homologous" refers to polynucleotides and polypeptides that retain functionality despite differences in primary structure from polynucleotides and polypeptides to which they are compared. For example, a polynucleotide substantially homologous to SEQ ID NO:2 is one that can secure expression in a host cell of a polypeptide product having at least a part of the primary structural conformation and the antigenic activity of the naturally-occurring protein having the amino acid sequence of SEQ ID NO:3, the polynucleotide selected from (a) polynucleotides that hybridize to SEQ ID NO:2 or fragments thereof and (b) polynucleotides that, but for the degeneracy of the genetic code, would hybridize to the polynucleotides defined in SEQ ID NO:2 and (a). By way of further example, a polypeptide substantially homologous to SEQ ID NO:3 is one that retains functionality as an antigen reactive with rheumatoid arthritis-associated antibodies although it may include additional amino acid residues or be a truncation, deletion variant, or substitution variant of SEQ ID NO:3. A substitution variant is one that contains a conservative substitution of one or more amino acid residues. A conservative substitution is a substitution of one amino acid residue for another wherein functionality of the peptide is retained, in this case, functionality as an antigen reactive with rheumatoid arthritis-associated antibodies. Amino acid residues belonging to certain conservative substitution groups can sometimes substitute for another amino acid residue in the same group. One such grouping is as follows: Pro, Ala, Gly; Ser, Thr; Asn, Gln; Asp, Glu; His; Lys, Arg; Cys; Ile, Leu, Met, Val; and Phe, Trp, Tyr. M. Jimenez-Montano & L. Zamora-Cortina, Evolutionary model for the generation of amino acid sequences and its application to the study of mammal alpha-hemoglobin chains, Proc. VIIth Int'l Biophysics Congress, Mexico City (1981). Other variations that are to be considered substantially homologous include substitution of D-amino acids for the naturally occurring L-amino acids, substitution of amino acid derivatives such as those containing additional side chains, and substitution of non-standard amino acids, i.e. α-amino acids that are rare or do not occur in proteins. The primary structure of a substantially homologous polypeptide is limited only by functionality.

A gene encoding a novel antigen ("RAMA") was molecularly cloned and expressed in bacterial and eukaryotic protein expression systems as described in U.S. patent application Ser. No. 08/019,780 filed Feb. 19, 1993, now U.S. Pat. No. 5,395,753, hereby incorporated by reference. Briefly, the steps involved in cloning and expressing the RAMA antigen are as follows. Polyadenylated mRNA was isolated from about $1\times10^8$ human Raji cells (ATCC no. CCL 86) using the "FAST TRACK" mRNA isolation kit (Invitrogen, San Diego, Calif.). The cells were lysed, homogenized, incubated with protease, and then subjected to oligo(dT) cellulose chromatography. The resulting polyadenylated RNA was then used as template material to prepare double-stranded cDNA using a commercial kit (λ Librarian, Invitrogen). The method used in this kit is the method described by Okayama and Berg, 2 Molecular and Cellular Biology 161 (1982), and Gubler and Hoffman, 25 Gene 263 (1983). The ends of the cDNA were made blunt-ended by treatment with T4 polymerase. EcoRI linkers were joined to the blunt-ended cDNA by T4 DNA ligase. The linkers had the following sequence:

```
5'-AATTCGCGGCCGC-3'          (SEQ ID NO:1)
     3'-GCGCCGGCG-5'
```

The 5' end of the shorter oligomer comprising the linker was phosphorylated whereas the 5' end of the longer oligomer (SEQ ID NO:1) was not. Once the linkers had been added, the cDNA was treated with T4 polynucleotide kinase to phosphorylate the protruding 5' end of the EcoRI linker. The double-stranded cDNA resulting from these procedures included a distribution of various lengths of cDNA as well as excess unreacted linkers. The unreacted linkers were removed and cDNA in the range of 1–5 kbp was selected by fractionating the cDNA by electrophoresis in an agarose gel. After fractionation was complete, the gel was removed from the gel apparatus, the cDNA was visualized with ethidium bromide, and slices of the cDNA lane were cut corresponding to the desired size of 1–5 kbp. The cDNA was immediately electroeluted.

The size-selected double-stranded cDNA was then cloned in the phage λgt11 cloning vector. R. Young & R. Davis, 80 Proc. Nat'l Acad. Sci USA 1194–98 (1983); T. Hyynh et al., in 1 *DNA Cloning: A Practical Approach* 49–78 (D. Glover, ed, IRL Press, Oxford, 1985). The EcoRI cloning site in this vector is located within the *E. coli* lacZ gene that was inserted into the phage λ DNA in making the λgt11 vector. The lacZ gene codes for the enzyme β-galactosidase. DNA fragments inserted into this gene by cloning at the EcoRI site result in fusion genes that make an inactive recombinant β-galactosidase enzyme under the control of the lac promoter. Recombinant phage can be recognized and selected by their inability to form blue-colored plaques on indicator plates containing the lactose analog 5-bromo-4-chloro-3-indolyl-β-D-galactoside (X-gal). Lambda gt11 phage are lac+ and thus able to cleave colorless X-gal into metabolites that self-assemble into a blue-colored indole compound. EcoRI-digested, dephosphorylated λgt11 DNA was obtained from Invitrogen.

Ligated DNA was then packaged in the "PACKAGENE" phage λ packaging system obtained commercially from Promega Corp. (Madison, Wis.), and the titer of recombinant phage was determined according to the supplier's instructions.

Recombinant antigen was isolated using a nonradioactive immunoblotting technique described in the technical manual for the "PROTOBLOT" Immunoscreening System from Promega Corp. Y1090 host cells were infected with $3 \times 10^4$ plaque forming units (PFU) of recombinant phage from the λgt11 library and then plated on agar plates. The plates were overlaid with dry nitrocellulose filters previously saturated with 10 mM IPTG and incubated at 37° C. During incubation, phage and proteins released from lyrically-infected cells adhered to the filters. The filters were removed from the plates and then blocked to prevent other proteins from adhering to the plates. Serum (diluted 1:20 with TBST buffer: 10 mM Tris.HCl, pH 8.0, 1 mM EDTA, 0.05% "TWEEN-20") from a patient clinically determined to have rheumatoid arthritis was then incubated with the filter. Then, the filter was washed in TBST to remove antibodies that were bound nonspecifically. Then the filter was incubated with an anti-IgM antibody-alkaline phosphatase conjugate (Kirkegaard & Perry Laboratories, Inc., Gaithersburg, Md.; diluted 1:100 with TBST). The filter was then washed again, and the color development substrates, nitro blue tetrazolium (NBT) and 5-bromo-4-chloro-3-indolyl phosphate (BCIP), were added. Positive plaques produced a dark purple color as a result of alkaline phosphatase activity. Positive plaques were retested and purified by replating until all of the plaques on a test plate yielded a positive signal.

A lysogen of a purified positive recombinant λgt11 phage was generated according to Technical Bulletin No. 006 of Promega Corp. Recombinant phage DNA was isolated from the λgt11 lysogen, using an alkaline lysis miniprep protocol described in T. Maniatis et al., *Molecular Cloning: A Laboratory Manual* (Cold Spring Harbor Laboratories, Cold Spring Harbor, N.Y., 1982). The DNA was digested with EcoRI, and the resulting DNA fragments were electrophoretically fractionated in a 0.7% low melting agarose gel. Upon ethidium bromide staining and ultraviolet illumination, a unique 2600 bp band was revealed. This band was sliced from the gel, and the agarose was melted at 70° C. The DNA was then phenol extracted and precipitated with alcohol.

The 2600 bp EcoRI fragment was then recloned, using standard procedures, e.g. J. Sambrook et al., *Molecular Cloning: A Laboratory Manual* (2d ed., 1989); T. Maniatis et al., *Molecular Cloning: A Laboratory Manual* (1982); F. Ausubel et al., *Current Protocols in Molecular Biology* (1987), at the EcoRI site of the plasmid expression vector "pTrcHis C," obtained from Invitrogen. This vector has the same reading frame as λgt11, contains all the DNA sequences to obtain high level protein expression in *E. coli*, and also contains a sequence encoding 6 consecutive histidine residues, which allow the expressed protein to bind Ni-charged "PROBOND" resin (Invitrogen) so that the recombinant protein can be easily purified in a one-step procedure. The pTrcHis C plasmid containing the 2600 bp fragment was transformed into *E. coli* strain Top10 (obtained from Invitrogen).

Expression of the recombinant protein was demonstrated by Western blot analysis. Transformants were grown in Luria Broth (LB) at 37° C. to an $OD_{600}$ of 0.5. Then isopropylthio-β-D-galactoside (IPTG), a gratuitous inducer of the lac operon, was added to a final concentration of 1 mM to induce expression of the recombinant protein. The transformants were grown an additional 3 hours at 30° C. after induction. Then about 200 µl of culture was placed in a microfuge tube and centrifuged briefly to pellet the cells. The broth was removed and discarded and the pellet was resuspended in SDS-containing buffer. T. Maniatis et al., supra. The samples were heated for 2 minutes in a boiling water bath and loaded on a 10% SDS-polyacrylamide gel and electrophoresed overnight at 70 volts. T. Maniatis et al., supra. The proteins were transferred electrophoretically to a nitrocellulose membrane using the "POLYBLOT" Electrotransfer System according to the instruction manual (American Bionetics, Inc., Hayward, Calif.). After transfer was complete, the membrane was removed and then blocked to prevent nonspecific binding of proteins. Serum (diluted 1:21) from a patient with rheumatoid arthritis was added to the membrane and incubated for 1 hour. The membrane was then washed in TBST. Then the membrane was incubated with anti-IgM antibody-alkaline phosphatase conjugate (Kirkegaard & Perry), as in the plaque screening procedure. The membrane was then washed in TBST, and color was developed by addition of NBT and BCIP.

These tests revealed a single band corresponding to a protein of about 48 kD that reacted with the reference serum. About 4 kD of the protein sequence is derived from the plasmid vector, suggesting that the remaining 44 kD of protein produced by the expression vector is from the antigen that reacts with serum from a rheumatoid arthritis patient.

SEQUENCING OF THE RECOMBINANT ANTIGEN GENE

The cloned cDNA was subjected to nucleotide sequence analysis according to the method of F. Sanger et al., *DNA Sequencing with Chain-Terminating Inhibitors*, 74 Proc. Nat'l Acad. Sci. USA 5463 (1977). An open reading frame comprising a 993 bp segment of DNA was revealed. This open reading frame (SEQ ID NO:2) encodes a 331 amino acid protein (SEQ ID NO:3) comprising the recombinant RAMA antigen of the instant invention.

PURIFICATION OF RECOMBINANT ANTIGEN FROM BACTERIA

The recombinant RAMA protein expressed by the bacterial plasmid expression vector was purified using an Invitrogen "PROBOND" column according to the instructions supplied with the column. About 1 liter of LB also containing glucose and 50 µg/ml ampicillin was inoculated with 10 ml of an overnight culture of BL21 cells (F' ompT hsdS$_B$ [r$_B^-$ m$_B^-$ dcm]) (a protease$^-$ strain, Novagen, Madison, Wis.) containing the expression plasmid. The cells were grown for 2.5 hours, at which time IPTG was added to a final concentration of 1 mM to induce expression of the recombinant RAMA protein. The cells were incubated an additional 3 hours at 37° C. after induction. Then the cells were harvested by centrifugation, resuspended, and lysed with lysozyme and sonication. The cells were then centrifuged at 10,000 rpm. The recombinant RAMA protein was soluble and remained in the supernatant.

Expression of the recombinant RAMA protein was confirmed by Western Blot analysis. After electrophoresis of a sample of recombinant RAMA protein in polyacrylamide gel and electrophoretic transfer to a nitrocellulose membrane, nonspecific binding of protein was blocked. Serum from a rheumatoid arthritis patient was added to the membrane-bound protein at a dilution of 1:21 and incubated for 1 hour. The membrane was then washed and incubated with anti-human IgM-alkaline phosphatase conjugate. The membrane was again washed before color development substrate solution was added. A single protein band with an $M_r$ of about 41,000 reacted with the serum from the rheumatoid arthritis patient. This is in reasonably good agreement with the predicted size of the RAMA protein (about 34 kd) based on the sequence.

EXPRESSION OF RECOMBINANT RAMA IN EUKARYOTIC CELLS

The 2600 bp DNA fragment containing the RAMA gene was recloned in the pBlueBacHis C baculovirus vector (Invitrogen) by standard methods. This pBlueBacHis C vector containing the RAMA gene was co-transfected with "BACULOGOLD" (Pharmingen, San Diego, Calif.) baculovirus DNA into *Spodoptera frugiperda* Sf9 cells. Homologous recombination between these DNAs resulted in a recombinant virus with the RAMA gene expressed under the control of the viral polyhedrin enhancer/promoter elements. The recombinant virus was produced in Sf9 insect cells and purified as described in the Invitrogen manual. The virus stock was then used to prepare 10-fold dilutions for plaque purification of recombinant virus according to the Invitrogen manual.

Expression of the RAMA gene in pBlueBacHis C was confirmed by Western Blot analysis. About 1 ml of Sf9 insect cells infected 3 days earlier with virus containing the recombinant plasmid were pelleted and dissolved in 100 µl of Laemmli buffer. U. Laemmli, 227 Nature 680–85 (1970). The sample was boiled for 2 minutes and then loaded on a 7.5% SDS-polyacrylamide gel and electrophoresed overnight at 70 volts, as described above. The protein was transferred electrophoretically to a nitrocellulose membrane and nonspecific binding of protein was blocked, as described above. Serum from a rheumatoid arthritis patient was added to the membrane-bound protein at a dilution of 1:21 and incubated for 1 hour. The membrane was then washed with TBST and incubated with anti-human IgM-alkaline phosphatase conjugate for 30 minutes. The membrane was again washed with TBST before color development substrate solution was added. A single protein band with an $M_r$ of about 100,000 reacted with the serum from the rheumatoid arthritis patient. The difference in $M_r$'s of the RAMA protein expressed in bacteria and in eukaryotic cells is believed due to glycosylation and perhaps other modifications of the expressed protein in eukaryotic cells. Recombinant RAMA protein produced by expression in this eukaryotic cell system was purified on a Ni-charged "PROBOND" column as described above. About 1.5 mg of protein was purified from 50 ml of culture.

ELISA TEST OF THE RECOMBINANT RAMA PROTEIN

About 100 µl of recombinant RAMA protein solution (1 µg/ml of purified recombinant protein in PBS buffer, pH 7.4), produced by expression in the *E. coli* system and purified on a "PROBOND" column, was placed in a well of a polystyrene microtiter plate (High binding 96 well Corning plate) and incubated overnight at 4° C. The plate was washed and then blocked overnight at 4° C. to prevent nonspecific binding. A 100 µl aliquot of serum diluted 1:21 was added to the well and incubated for 1 hour, and then the well was washed. A 100 µl aliquot of alkaline phosphatase-conjugated anti-human IgM (Kirkegaard & Perry) was added to the well and incubated for 1 hour, and then the well was washed again. Then 100 µl of alkaline phosphatase substrate, prepared by adding 5 mg of p-nitrophenolphosphate and 1 ml of 5× diethanolamine buffer (supplied by Kirkegaard and Perry) to 4 ml of distilled water, was added to the well and incubated at 37° C. for 15 minutes. Then, the optical density was measured at 405 nm.

Sera from 60 patients with clinical symptoms of rheumatoid arthritis (35 were seropositive and 25 were seronegative for Rf), 20 individuals seropositive for an anti-DNA disease marker for SLE, and 20 healthy individuals were tested by the method outlined above. The results of these tests are summarized in FIG. 1 and the following table.

| Serum | Total | RAMA+ | RAMA− | Percent |
|---|---|---|---|---|
| Rf+ | 35 | 34 | 1 | 97 |
| Rf− | 25 | 11 | 14 | 44 |
| Anti-DNA+ | 20 | 3 | 17 | 15 |
| Healthy | 20 | 0 | 20 | 0 |

Serum from all of the healthy subjects showed ELISA values below 0.250. Thus, a reading of 0.250 was taken as the cut-off value to determine a positive reaction. Of the 35 sera from seropositive rheumatoid arthritis patients, 34, or 97%, showed ELISA values above 0.250 and, thus, were deemed to give a positive reaction. Of the 25 sera from seronegative rheumatoid arthritis patients, 11, or 44%, showed ELISA values above 0.250 and, thus, were deemed to give a positive reaction. Three of the 20 Anti-DNA+ control sera also gave positive reactions. Therefore, these results show that almost all seropositive rheumatoid arthritis patients could be diagnosed with the aid of this ELISA test to detect the presence of antibodies in the serum against the RAMA recombinant antigen. Further, almost half of seronegative rheumatoid arthritis patients could be diagnosed as well. These results suggest that about 85% of rheumatoid arthritis cases could be diagnosed using this invention as compared to only about 70% using the standard Rf test.

Additional tests were conducted to demonstrate that RAMA is not Rf. An independent reference laboratory was contracted to conduct the standard Rf aggregation test using the recombinant RAMA protein. No aggregates of IgG were formed. This is a negative result, inasmuch as aggregates did form when Rf was assayed in the same manner as a positive control. Further, recombinant RAMA antigen was attached to the wells of a microtiter plate, and the bound RAMA antigen was then exposed to an enzyme-conjugated IgG antibody. A colorimetric assay of enzyme activity was conducted as described above. No enzyme activity was detected, indicating that the IgG antibody failed to bind to the RAMA protein. Finally, 7 clinically normal subjects exhibiting a positive result when tested by ELISA for reaction with Rf, i.e. all 7 subjects were seropositive for Rf, were tested by ELISA with RAMA as the primary antigen. All 7 were seronegative for reaction with RAMA. These results demonstrate that the recombinant RAMA antigen that is the subject of the invention is not Rf.

PEPTIDES WITH RAMA ACTIVITY

The scope of the present invention includes any peptide having the activity of a RAMA peptide. Such a peptide can include recombinant RAMA as in SEQ ID NO:3, and peptides substantially homologous thereto. An example of a peptide substantially homologous to the naturally-occurring RAMA is the recombinant RAMA described above, wherein 6 histidine residues were added to facilitate purification of the protein by affinity chromatography using a metal-containing resin. Despite the addition of the 6 histidine residues, the recombinant RAMA was reactive with the rheumatoid arthritis-associated IgM antibodies. Peptides that are substantially homologous to RAMA can be synthesized by expression in host cells, as exemplified above, or by chemical synthesis.

Short peptides for detecting rheumatoid arthritis-associated antibodies can be identified and prepared as follows. Endoproteinase-lys C (Boehringer Mannheim) is used according the supplier's directions to digest the RAMA protein into peptide fragments. These fragments are fractionated by HPLC and sequenced according to the method of N. Legendre & P. T. Matsudaira, *Gel Electrophoresis, in A Practical Guide to Protein and Peptide Purification for Microsequencing* 52–66 (P. T. Matsudaira, ed., 1989). Additional fragments are prepared by proteinase digestion of RAMA and separation on polyacrylamide gels. J. Sambrook et al., *Molecular Cloning: A Laboratory Manual* (2d ed., 1989). These fragments are subjected to Western blotting, H. Towbin et al., *Electrophoretic Transfer of Proteins from Polyacrylamide Gels to Nitrocellulose Sheets: Procedure and Some Applications*, 76 Proc. Nat'l Acad. Sci. USA 4350 (1979), with identification of fragments bound by rheumatoid arthritis-associated antibodies. Those peptides reacting with the antibodies are sequenced. Following identification of the fragment or fragments of RAMA having epitopes recognized by the rheumatoid arthritis-associated antibodies, the process of digestion with a proteinase, Western blotting, and sequencing is repeated using a different proteinase to yield smaller peptides. This procedure leads to identification of a sequence recognized by the antibodies. From these data, oligopeptides with similar sequence are synthesized by chemical synthesis, B. Merrifield, 85 J. Am. Chem. Soc. 2149–2156 (1963); B. Merrifield et al., 21 Biochemistry 5020–31 (1982); Houghten, 82 Proc. Nat'l Acad. Sci. USA 5131–35 (1985), hereby incorporated by reference, or biotechnological methods, J. Sambrook et al., *Molecular Cloning: A Laboratory Manual* (2d ed., 1989), and tested for reactivity to the rheumatoid arthritis-associated antibodies. Several peptidomimetic inhibitors of enzymes have been described using these techniques. A. Smith et al., *Design and Synthesis of Peptidomimetic Inhibitors of HIV-1 Protease and Renin: Evidence for Improved Transport*, 37 J. Med. Chem. 215 (1994); S. Francis et al., *Molecular Characterization and Inhibition of a Plasmodium falciparum Aspartic Hemoglobinase*, 13 EMBO J. 306 (1994); A. Garcia et al., *Peptidomimetic Inhibitors of Ras Farnesylation and Function in Whole Cells*, 268 J. Biol. Chem. 18415 (1993).

DEPOSIT OF BIOLOGICAL MATERIAL

A deposit of an *E. coli* strain containing a plasmid bearing a gene encoding the recombinant RAMA antigen described herein and used for diagnosing rheumatoid arthritis was deposited on Apr. 13, 1994, with the following International Depository Authority: American Type Culture Collection, 12301 Parklawn Drive, Rockville, Md. 20852 USA. The accession number of the deposited strain is ATCC 69605.

---

I claim:

1. An antigen for diagnosing rheumatoid arthritis comprising a peptide having an amino acid sequence identified as SEQ ID NO:3, wherein said antigen is reactive with rheumatoid arthritis-associated antibodies.

2. The antigen of claim 1 wherein said peptide is produced by expression of a recombinant gene in a host cell.

3. The antigen of claim 2 wherein said host cell is a prokaryotic cell.

4. The antigen of claim 3 wherein said host cell is *E. coli*.

5. The antigen of claim 2 wherein said host cell is a eukaryotic cell.

6. The antigen of claim 1 wherein said polypeptide is produced by chemical synthesis.

7. The antigen of claim 1 wherein said rheumatoid arthritis-associated antibodies are IgM antibodies.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 13 nucleotides
        ( B ) TYPE: nucleic acid
        ( C ) STRANDEDNESS: single
        ( D ) TOPOLOGY: linear ( i i ) MOLECULE TYPE: synthetic linker ( x i ) SEQUENCE DESCRIPTION: SEQ ID NO:1:

AATTCGCGGC CGC    13

( 2 ) INFORMATION FOR SEQ ID NO:2:

( i ) SEQUENCE CHARACTERISTICS:
        ( A ) LENGTH: 993 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
ACT  TCA  GTT  AAT  TCT  GCA  GAA  GCC  AGC  ACT  AGT  GCT  AAC  TCT  GTA  ACT    48
Thr  Ser  Val  Asn  Ser  Ala  Glu  Ala  Ser  Thr  Ser  Ala  Asn  Ser  Val  Thr
 1             5                        10                       15

TGT  ACA  TTT  TCC  CAT  GGA  TAT  GAA  AAG  CCT  GAA  GAA  TTG  TGG  ATC  CCC    96
Cys  Thr  Phe  Ser  His  Gly  Tyr  Glu  Lys  Pro  Glu  Glu  Leu  Trp  Ile  Pro
               20                       25                       30

TTT  TCT  CCC  GCA  GCG  AGT  AGC  TGC  CAC  AAT  GCC  AGT  GGA  AAG  GTT  GCA   144
```

```
Phe Ser Pro Ala Ala Ser Ser Cys His Asn Ala Ser Gly Lys Glu Ala
    35                      40                  45

AAG GTT TGC ACC ATC AGT CCC TTG AGC TCC TTG ATT CCT GAA GCA GAA  192
Lys Val Cys Thr Ile Ser Pro Leu Ser Ser Leu Ile Pro Glu Ala Glu
    50                      55                  60

GAT AGC TGG TGG ACG GGG GAT TCT GCT AGT CTC GAC ACG GCA GGC ATC  240
Asp Ser Trp Trp Thr Gly Asp Ser Ala Ser Leu Asp Thr Ala Gly Ile
65                      70                  75                  80

AAA CTC ACA GTT CCA ATC GAG AAG TTC CCC GTG ACA ACG GAG ACG TTT  288
Lys Leu Thr Val Pro Ile Glu Lys Phe Pro Val Thr Thr Gln Thr Phe
                85                  90                  95

GTC GTC GGT TGC ATC AAG GGA GAG GAC GCA CAG AGT TGT ATG GTC ACG  336
Val Val Gly Cys Ile Lys Gly Asp Asp Ala Gln Ser Cys Met Val Thr
            100                     105                 110

GTG ACA GTA CAA GCC AGA GCC TCA TCG GTC GTC AAT AAT GTC GCA AGG  384
Val Thr Val Gln Ala Arg Ala Ser Ser Val Val Asn Asn Val Ala Arg
            115                     120                 125

TGC TCC TAC GCT GCA GAC AGC ACT CTT GGT CCT GTC AAG TTC TCT GCG  432
Cys Ser Tyr Gly Ala Asp Ser Thr Leu Gly Pro Val Lys Leu Ser Ala
        130                     135                 140

GAA GGA CCC ACT ACA ATG ACC CTC GTC TGC GGG AAA GAT GGA GTC AAA  480
Glu Gly Pro Thr Thr Met Thr Leu Val Cys Gly Lys Asp Gly Val Lys
145                     150                 155                 160

GTT CCT CAA GAC AAC AAT CAG TAC TGT TCC GGG ACG ACG CTG ACT GGT  528
Val Pro Gln Asp Asn Asn Gln Tyr Cys Ser Gly Thr Thr Leu Thr Gly
                165                 170                 175

TGC AAC GAG AAA TCG TTC AAA GAT ATT TTG CCA AAA TTA ACT GAG AAC  576
Cys Asn Glu Lys Ser Phe Lys Asp Ile Leu Pro Lys Leu Thr Glu Asn
            180                     185                 190

CCG TCG CAG GGT AAC GCT TCG AGT GAT AAG GGT GCC ACG CTA ACG ATC  624
Pro Trp Gln Gly Asn Ala Ser Ser Asp Lys Gly Ala Thr Leu Thr Ile
            195                     200                 205

AAG AAG GAA GCA TTT CCA GCC GAG TCA AAA AGC GTC ATT ATT GGA TGC  672
Lys Lys Glu Ala Phe Pro Ala Glu Ser Lys Ser Val Ile Ile Gly Cys
    210                     215                 220

ACA GGG GGA TCG CCT GAG AAG CAT CAC TGT ACC GTG AAA CTG GAG TTT  720
Thr Gly Gly Ser Pro Glu Lys His His Cys Thr Val Lys Leu Glu Phe
225                     230                 235                 240

GCC GGG GCT GCA GGG GGC GCC GGG GGT GGA CGA GGA GGA GCA GCC GGT  768
Ala Gly Ala Ala Gly Gly Ala Gly Gly Gly Gly Gly Gly Ala Ala Gly
                245                 250                 255

GGA GCC GGG GGC GCC GCG GCT GCC GGC GGA GCA GGA GCA GGC GGA GGG  816
Gly Ala Gly Gly Ala Ala Ala Ala Gly Gly Ala Gly Ala Gly Gly Gly
            260                     265                 270

GCT GGT ACC GAC ACA GAT AAA TAT GTC ACA GGA ATA AAT GCC TCT CAT  864
Ala Gly Thr Asp Thr Asp Lys Tyr Val Thr Gly Asn Ala Ile Ser His
        275                     280                 285

GGT CAG ACC ACT TAT GGT AAC GCT GAA GAC AAA GAG TAT CAG CAA GAA  912
Gly Gln Thr Thr Tyr Gly Asn Ala Glu Asp Lys Glu Tyr Gln Gln Glu
    290                     295                 300

TTC GTG GGA ATT ATG ACA GTA ACT ATG ACA TTT AAA TTG GGG CCC CGT  960
Phe Val Gly Ile Met Thr Val Thr Met Thr Phe Lys Leu Gly Pro Arg
305                     310                 315                 320

AAA GCT ACG GGA CGG TGG AAT CCT CAA CCT GGA                      993
Lys Ala Thr Gly Arg Trp Asn Pro Gln Pro Gly
                325                 330
```

( 2 ) INFORMATION FOR SEQ ID NO:3:

( i ) SEQUENCE CHARACTERISTICS:
        ( A ) LENGTH: 331 amino acids (B) TYPE: amino acid
(D) TOPOLOGY: linear (xi) SEQUENCE DESCRIPTION: SEQ ID NO:3:

```
Thr Ser Val Asn Ser Ala Glu Ala Ser Thr Ser Ala Asn Ser Val Thr
 1               5                  10                  15
Cys Thr Phe Ser His Gly Tyr Glu Lys Pro Glu Glu Leu Trp Ile Pro
             20                  25                  30
Phe Ser Pro Ala Ala Ser Ser Cys His Asn Ala Ser Gly Lys Glu Ala
         35                  40                  45
Lys Val Cys Thr Ile Ser Pro Leu Ser Ser Leu Ile Pro Glu Ala Glu
     50                  55                  60
Asp Ser Trp Trp Thr Gly Asp Ser Ala Ser Leu Asp Tyr Ala Gly Ile
 65                  70                  75                  80
Lys Leu Thr Val Pro Ile Glu Lys Phe Pro Val Thr Thr Gln Thr Phe
                 85                  90                  95
Val Val Gly Cys Ile Lys Gly Asp Asp Ala Gln Ser Cys Met Val Thr
             100                 105                 110
Val Thr Val Gln Ala Arg Ala Ser Ser Val Val Asn Asn Val Ala Arg
         115                 120                 125
Cys Ser Tyr Gly Ala Asp Ser Thr Leu Gly Pro Val Lys Leu Ser Ala
     130                 135                 140
Glu Gly Pro Thr Thr Met Thr Leu Val Cys Gly Lys Asp Gly Val Lys
145                 150                 155                 160
Val Pro Gln Asp Asn Asn Gln Tyr Cys Ser Gly Thr Thr Leu Thr Gly
             165                 170                 175
Cys Asn Glu Lys Ser Phe Lys Asp Ile Leu Pro Lys Leu Thr Glu Asn
         180                 185                 190
Pro Trp Gln Gly Asn Ala Ser Ser Asp Lys Gly Ala Thr Leu Thr Ile
     195                 200                 205
Lys Lys Glu Ala Phe Pro Ala Glu Ser Lys Ser Val Ile Ile Gly Cys
 210                 215                 220
Thr Gly Gly Ser Pro Glu Lys His His Cys Thr Val Lys Leu Glu Phe
225                 230                 235                 240
Ala Gly Ala Ala Gly Gly Ala Gly Gly Gly Gly Gly Gly Ala Ala Gly
             245                 250                 255
Gly Ala Gly Gly Ala Ala Ala Ala Gly Gly Ala Gly Ala Gly Gly Gly
         260                 265                 270
Ala Gly Thr Asp Thr Asp Lys Tyr Val Thr Gly Asn Ala Ile Ser His
     275                 280                 285
Gly Gln Thr Thr Tyr Gly Asn Ala Glu Asp Lys Glu Tyr Gln Gln Glu
 290                 295                 300
Phe Val Gly Ile Met Thr Val Thr Met Thr Phe Lys Leu Gly Pro Arg
305                 310                 315                 320
Lys Ala Thr Gly Arg Trp Asn Pro Gln Pro Gly
             325                 330
```